US00PP28691P3

(12) United States Plant Patent
De Jong

(10) Patent No.: US PP28,691 P3
(45) Date of Patent: Nov. 21, 2017

(54) ***SUTERA* PLANT NAMED 'SUTZ0001'**

(50) Latin Name: *Sutera cordata*
Varietal Denomination: SUTZ0001

(71) Applicant: SYNGENTA PARTICIPATIONS AG, Basel (CH)

(72) Inventor: Erwin De Jong, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/757,091

(22) Filed: Nov. 16, 2015

(65) Prior Publication Data

US 2016/0174451 P1 Jun. 16, 2016

Related U.S. Application Data

(60) Provisional application No. 62/091,775, filed on Dec. 15, 2014.

(51) Int. Cl.
*A01H 5/02* (2006.01)

(52) U.S. Cl.
USPC ..... Plt./485

(58) Field of Classification Search
USPC ..... Plt./485
CPC ..... A01H 5/02
See application file for complete search history.

(56) References Cited

PUBLICATIONS

GTITM UPOVROM Citation For 'SUTZ0001' as per CA PBR 12-7776; Oct. 30, 2012; 1 page.*

* cited by examiner

*Primary Examiner* — Kent L Bell
(74) *Attorney, Agent, or Firm* — Dale Skalla

(57) ABSTRACT

A new *Sutera* plant named 'SUTZ0001' particularly distinguished by large, white flowers, medium green foliage, medium to large sized, deltoid rounded leaves, fair branching, mounding and semi-trailing trailing plant habit.

2 Drawing Sheets

Latin name of the genus and species of the plant claimed: *Sutera cordata.*

Varietal denomination: 'SUTZ0001'.

BACKGROUND OF THE NEW PLANT

The present invention comprises a new *Sutera*, botanically known as *Sutera cordata*, and hereinafter referred to by the variety name 'SUTZ0001'.

'SUTZ0001' is a product of a planned breeding program. The new cultivar has large, white flowers, medium green foliage, medium to large sized, deltoid rounded leaves, fair branching, mounding and semi-trailing trailing plant habit.

'SUTZ0001' originated from a cross conducted during the summer of 2008 between a proprietary line designated 'L0001-1' as the female parent, and a proprietary line designated 'K0006-4' as the male parent. 'L0001-1' is a white flowering selection with smaller flowers than 'SUTZ0001' and less branching, 'K0006-4' is a white flowering selection with comparable size flowers, later flowering and with relatively poor heat resistance.

The resultant seed was sown in a greenhouse in Enkhuizen, Netherlands in early spring of 2009. In late spring of 2009, 'SUTZ0001' was selected as one flowering plant within the progeny of the stated cross in the same place.

The first act of asexual reproduction of 'SUTZ0001' was accomplished when vegetative cuttings were propagated from the initial selection in May 2009 in a controlled environment in Enkhuizen, Netherlands.

BRIEF SUMMARY OF INVENTION

Horticultural examination of plants grown from cuttings of the plant initiated in June 2009, and continuing thereafter indoors and outdoors in Andijk and Enkhuizen, The Netherlands, Sarrians, France, and in Gilroy, Calif., United States, have demonstrated that the combination of characteristics as herein disclosed for 'SUTZ0001' are firmly fixed and are retained through successive generations of asexual reproduction.

'SUTZ0001' has not been observed under all possible environmental conditions. The phenotype may vary significantly with variations in environment such as temperature, light intensity and day length.

Plant Breeder's Rights for this cultivar were applied for in Canada on Oct. 30, 2012, No. 12-7776 and in the European Union at CPVO on Jan. 10, 2014, No. 2014/0069. 'SUTZ0001' has not been made publicly available more than one year prior to the filing of this application.

The following traits have been repeatedly observed and are determined to be basic characteristics of the new variety. The combination of these characteristics distinguishes this *Sutera* as a new and distinct variety.

BRIEF DESCRIPTION OF THE PHOTOGRAPHS

The accompanying photographic drawing shows typical flower and foliage characteristics of 'SUTZ0001' with colors being as true as possible with an illustration of this type.

Figure 1:
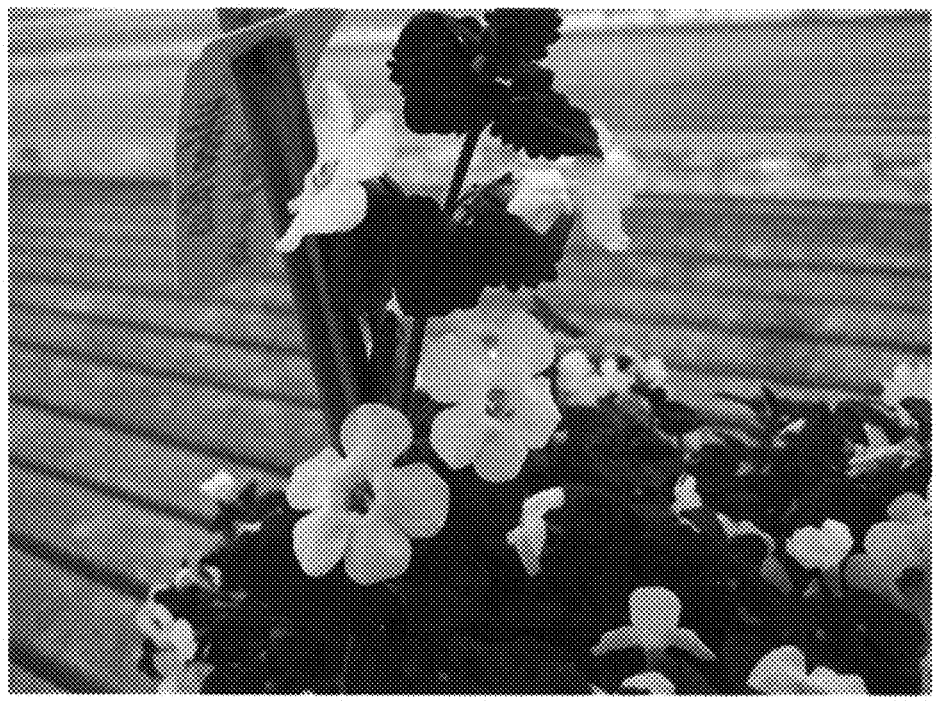

FIG. 1 shows a close view of a flowering shoot, and

Figure 2:
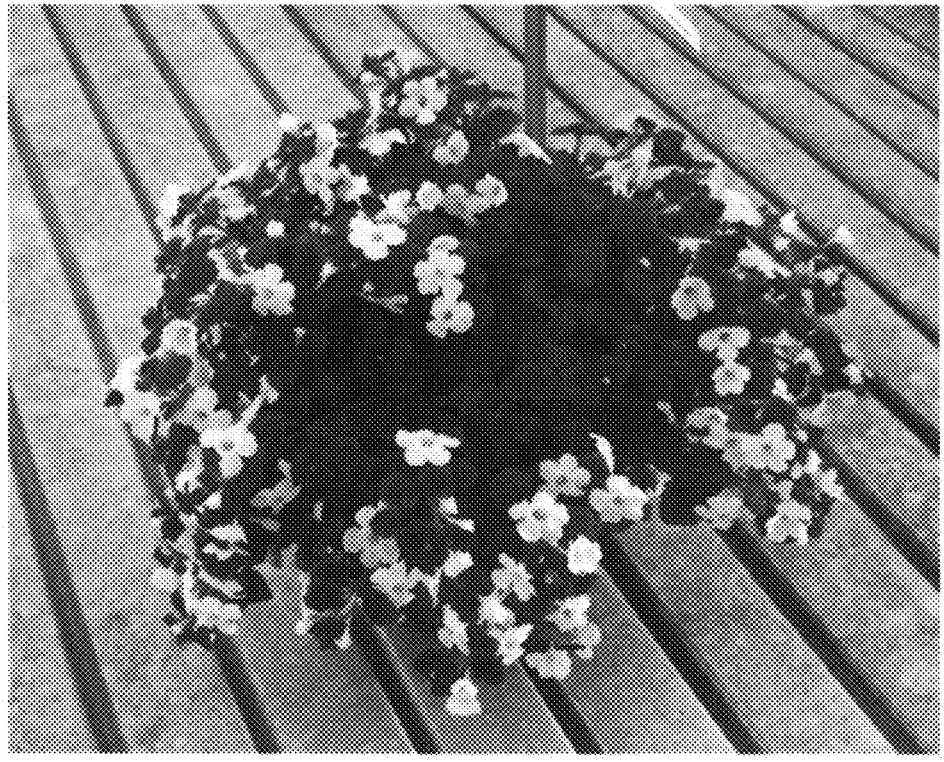

FIG. 2 a whole flowering plant.

Figure 3:
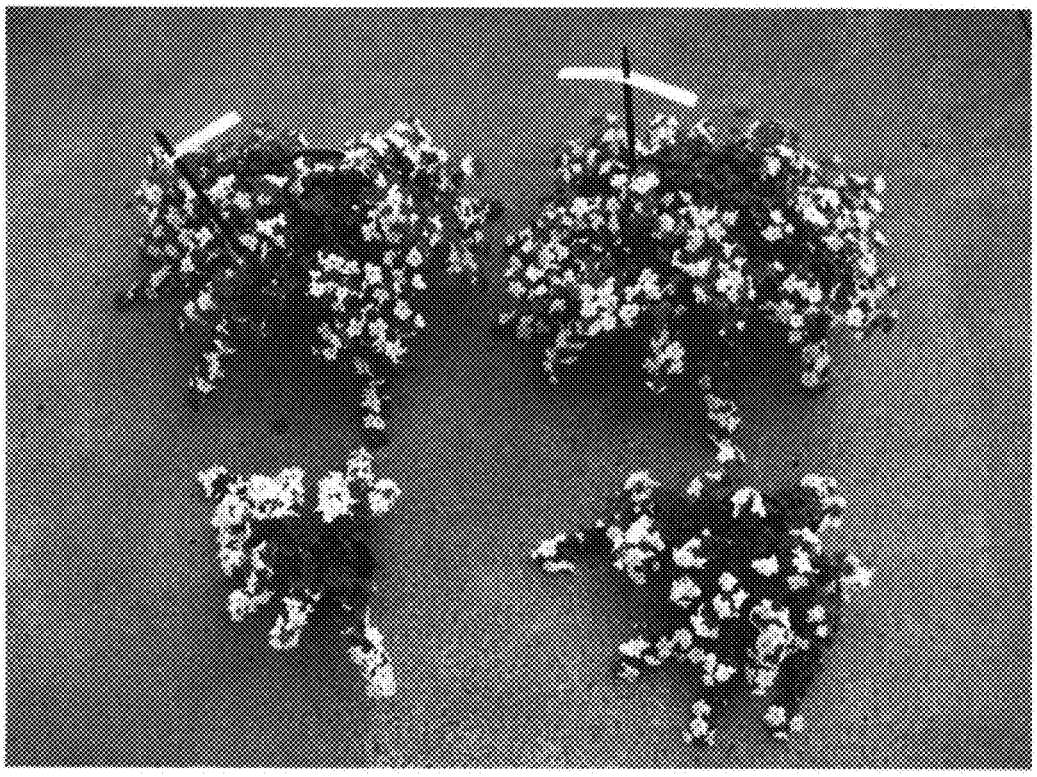

FIG. 3 shows a comparison between 'Cays Juwit09' and 'SUTZ0001'.

DETAILED BOTANICAL DESCRIPTION

The following observations, measurements, and comparisons were taken indoors in Enkhuizen, Netherlands in mid November 2014 using plants in 19 cm pots from the Elite stock. The plant in the 19 cm pot is originally stuck as unrooted cutting in week 20 (mid May 2014) in Enkhuizen and 4-5 weeks later potted up directly in 19 cm pot, 1 plant/pot.

FIGS. 1 and 2 were taken in November 2014 of a plant in a 19 cm pot from in a greenhouse in Enkhuizen, The Netherlands.

FIG. 3 was taken in April 2012 in a greenhouse in Andijk, The Netherlands. The plants were respectively grown in 10.5 cm pot and a big pot holding 3 plants. The plants were approximately 13 weeks old: candidate on the right hand, comparison 'Cays Juwit09' on the left side.

Color references are made to The Royal Horticultural Society Colour Chart (R.H.S.) 2001.

TABLE 1

DIFFERENCES BETWEEN THE NEW VARIETY 'SUTZ0001' AND MOST SIMILAR VARIETIES

| | 'SUTZ0001' | 'BALABOWITE' (U.S. Plant Pat. No. 19,080), also known as 'Abunda Colossal White' |
|---|---|---|
| Corolla diameter: | 2.5-2.7 cm | Smaller, about 2.1-2.2 cm |
| Stem, length of internodes: | Shorter | Distinctly longer |
| Foliage color: | Medium green | Deeper green |
| | 'SUTZ0001' | 'CAY JUWIT09', also known as 'Calypso Jumbo White 09', U.S. Plant Pat. No. 21,197 |
| Branching characteristics: | More branches | Fewer branches |
| Growth vigor: | About medium | Weak to medium |
| | 'SUTZ0001' | 'Gulliver Dynamic White' |
| Branching characteristics: | Fewer branches | Stronger branching |

Plant:

*Growth and habit.*—Medium vigor, fair branching with relatively thick stems, initially spreading later mounding to trailing.

*Height.*—15-20 cm (above soil).

*Width (diameter).*—40-45 cm, including flowers.

*Spread (including flowers).*—1 main branch in 19 cm pot measures 18-22 cm length.

*Number of branches.*—25-30.

*Time to produce a finished flowering plant.*—12-13 weeks for 12 cm pot, 10-11 weeks for 10.5 or 11 cm pot.

*Outdoor plant performance.*—Used for hanging baskets or in mixed container plantings.

*Time to initiate and develop roots.*—21 days at 19-22° C.

Roots:

*Number of days to initiate and develop roots.*—About 18-21 days at about 21 degrees C.

*Type.*—Fine, fibrous, free branching.

*Color.*—RHS N155B but whiter.

Stem:

*Characteristics.*—Cross section round, fair degree of self-branching.

*Stem length.*—18-22 cm.

*Diameter.*—0.2 cm.

*Internode length.*—2.2-2.4 cm.

*Color.*—RHS 140A, no anthocyanin.

*Texture.*—Pubescent, canescent.

Foliage:

*Arrangement.*—Opposite, decussate.

*Leaf shape.*—Initially deltoid, later nearly round.

*Apex.*—Acute.

*Base.*—Truncate, sometimes auriculate.

*Margin.*—Dentate.

*Leaf length.*—Up to 2.5 cm.

*Leaf width.*—Up to 2.8 cm.

*Immature leaf, color upper surface.*—RHS N134B.

*Immature leaf, color lower surface.*—RHS N134D.

*Mature color upper surface.*—RHS N134B.

*Mature color lower surface.*—RHS N134D.

*Venation type.*—Palmate.

*Venation color.*—RHS 134B.

*Texture.*—Both surfaces have a bit of puberulous texture.

Petiole:

*Length.*—0.6 cm.

*Petiole width.*—Up to 2 mm.

*Petiole color.*—RHS N134B.

*Texture.*—Pubescent.

Inflorescence:

*Blooming habit.*—Flowers continuously through the growing season from spring to fall as long as temperatures don't exceed 25° Centigrade.

*Type of inflorescence.*—Solitary, flowers emerge from the leaf axils of the upper stem nodes, usually 2 flowers per node.

*Quantity of flowers per stem.*—About 8-10 flowers and additional buds in a cluster at the end of the stem.

*Fragrance.*—None.

Pedicel:

*Color.*—RHS 134A.

*Length.*—0.8-1.0 cm.

*Diameter.*—0.1 cm.

*Texture.*—Dense pubescence.

Flower:

*Corolla type and shape.*—Single-type, formed by 5 partly fused petals. Upper part is nearly round, salver-shaped with partly free petal lobes, while lower part is funnel-shaped formed by the 5 fused petals.

*Corolla diameter.*—2.5-2.7 cm.

*Flower length.*—About 1.7 cm.

*Funnel diameter.*—0.5-0.6 cm.

*Color upper surface.*—Whiter than RHS N155B.

*Color lower surface.*—Whiter than RHS N155B.

*Color of throat.*—Deep yellow, RHS 23A.

*Color of funnel outer side.*—RHS 17B.

*Texture, upper surface.*—Smooth and glabrous.

*Texture, lower surface.*—Very short pubescence, increasing towards the corolla tube.

Petals (free lobes):

*Apex.*—Rounded.

*Base.*—Fused.

*Margin.*—Entire.

*Length of lobes (from the corolla opening).*—1.2 cm.

*Width of lobes.*—10-12 mm.

Flower buds:

*Shape.*—Cone-shaped.

*Diameter.*—0.5-0.7 cm.

*Length.*—1.4-1.6 cm.

*Color (at tight bud).*—Greenish-white, RHS 150D.

Calyx:

*Shape.*—5 sepals in a whorl around the flower tube.

*Sepal shape*.—Lanceolate, fused at the base.

*Sepal color*.—RHS 137C to 137D upper and lower.

*Length.*—0.5-0.6 cm.

*Width.*—About 1 mm.

*Apex*.—Acuminate.

*Base*.—Fused.

*Texture.*—Covered with dense hair, mainly on the outer side.

Reproductive organs:

Stamens:

*Quantity.*—4.

*Filament, color*.—White, RHS N155B.

*Length.*—1.2-1.4 cm.

*Diameter.*—0.1 cm.

*Anther color*.—Yellow, RHS 12A.

*Pollen amount*.—Moderate.

*Pollen color*.—Yellow, RHS 12A.

Pistil:

*Quantity per flower*.—One.

*Length.*—1.1-1.3 cm.

*Stigma color*.—Light green, RHS N144D.

*Style color*.—Greenish white, RHS 144D.

Fruit and seed set: Has not been observed.

Disease and insect resistance: Resistance and susceptibility typical for the species, no special observations made.

What is claimed is:

1. A new and distinct cultivar of *Sutera* plant named 'SUTZ0001' substantially as illustrated and described herein.

* * * * *